US012580076B2

(12) United States Patent
Sekine et al.

(10) Patent No.: US 12,580,076 B2
(45) Date of Patent: Mar. 17, 2026

(54) MEDICAL DEVICE HAVING COMMMUNICATION FUNCTION AND COMMUNICATION SYSTEM

(71) Applicant: TERUMO KABUSHIKI KAISHA, Tokyo (JP)

(72) Inventors: Yusuke Sekine, Chigasaki (JP); Yuki Sakaguchi, Isehara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 774 days.

(21) Appl. No.: 17/896,327

(22) Filed: Aug. 26, 2022

(65) Prior Publication Data

US 2022/0415494 A1     Dec. 29, 2022

Related U.S. Application Data

(63) Continuation of application No. PCT/JP2021/002983, filed on Jan. 28, 2021.

(30) Foreign Application Priority Data

Feb. 27, 2020     (JP) ................................. 2020-032305

(51) Int. Cl.
*G16H 40/40*          (2018.01)
*A61B 90/00*          (2016.01)
(Continued)

(52) U.S. Cl.
CPC .............. G16H 40/40 (2018.01); A61B 90/37 (2016.02); A61B 90/98 (2016.02); G16H 40/63 (2018.01)

(58) Field of Classification Search
CPC ........ G16H 40/40; G16H 40/63; G16H 20/10; G16H 10/60; G16H 20/40; G16H 10/00;
(Continued)

(56) References Cited

U.S. PATENT DOCUMENTS

| | | | |
|---|---|---|---|
| 2006/0016897 A1* | 1/2006 | Yasuda | .................. A61B 50/30 235/492 |
| 2010/0069833 A1 | 3/2010 | Wenderow et al. | |

(Continued)

FOREIGN PATENT DOCUMENTS

| | | |
|---|---|---|
| JP | 2003016198 A | 1/2003 |
| JP | 2003263495 A | 9/2003 |

(Continued)

OTHER PUBLICATIONS

Office Action (Notice of Reasons for Refusal) issued on Jun. 4, 2024, in corresponding Japanese Patent Application No. 2022-503184 and English translation of the Office Action. (10 pages).

(Continued)

*Primary Examiner* — Jason E Flick
(74) *Attorney, Agent, or Firm* — Buchanan Ingersoll & Rooney PC

(57)          ABSTRACT

A medical device having a communication function that includes an information reading section configured to read, from an additional medical device, information regarding medical care, and a communication section configured to transmit the information read by the information reading section.

15 Claims, 3 Drawing Sheets

START

S1 | ALLOW MEDICAL INSTRUMENT TO READ INFORMATION

S2 | DISPLAY RESULT OF READING

S3 | READ INFORMATION REGARDING SURGICAL MANIPULATION

S4 | TRANSMIT INFORMATION TO HIS

S5 | STORE INFORMATION IN HIS

END

(51) Int. Cl.
    *A61B 90/98*         (2016.01)
    *G16H 40/63*         (2018.01)
(58) Field of Classification Search
    CPC ........ G16H 20/00; G16H 40/00; G16H 10/65;
                 G16H 40/60; G16H 20/13; G16H 20/17;
                 G16H 70/00; A61B 90/37; A61B 90/98;
                 A61B 90/90; A61B 2017/00221; A61J
                 2205/60; A61M 2205/52; A61M
                 2205/6063; A61M 2205/60; A61M
                 2205/6072
    See application file for complete search history.

(56) References Cited

U.S. PATENT DOCUMENTS

| | | |
|---|---|---|
| 2017/0035523 A1 | 2/2017 | Kerns et al. |
| 2017/0258986 A1 | 9/2017 | Tsoukalis |
| 2017/0333105 A1 | 11/2017 | Newell et al. |

FOREIGN PATENT DOCUMENTS

| | | |
|---|---|---|
| JP | 2006039773 A | 2/2006 |
| JP | 2010524593 A | 7/2010 |
| JP | 2016-140644 A | 8/2016 |
| JP | 2017093941 A | 6/2017 |
| JP | 2017205546 A | 11/2017 |
| JP | 2019-517852 A | 6/2019 |

OTHER PUBLICATIONS

Office Action (Notice of Reasons for Refusal) issued on Dec. 3, 2024, in corresponding Japanese Patent Application No. 2022-503184 and machine English translation of the Office Action. (12 pages).

International Search Report (PCT/ISA/210) with translation and Written Opinion (PCT/ISA/237) mailed on Apr. 6, 2021, by the Japan Patent Office as the International Searching Authority for International Application No. PCT/JP2021/002983. (10 pages).

English Translations of the International Search Report (Form PCT/ISA/210) and the Written Opinion of the International Searching Authority (Form PCT/ISA/237) issued Apr. 6, 2021, by the Japan Patent Office in corresponding International Application No. PCT/JP2021/002983. (6 pages).

* cited by examiner

F I G . 1
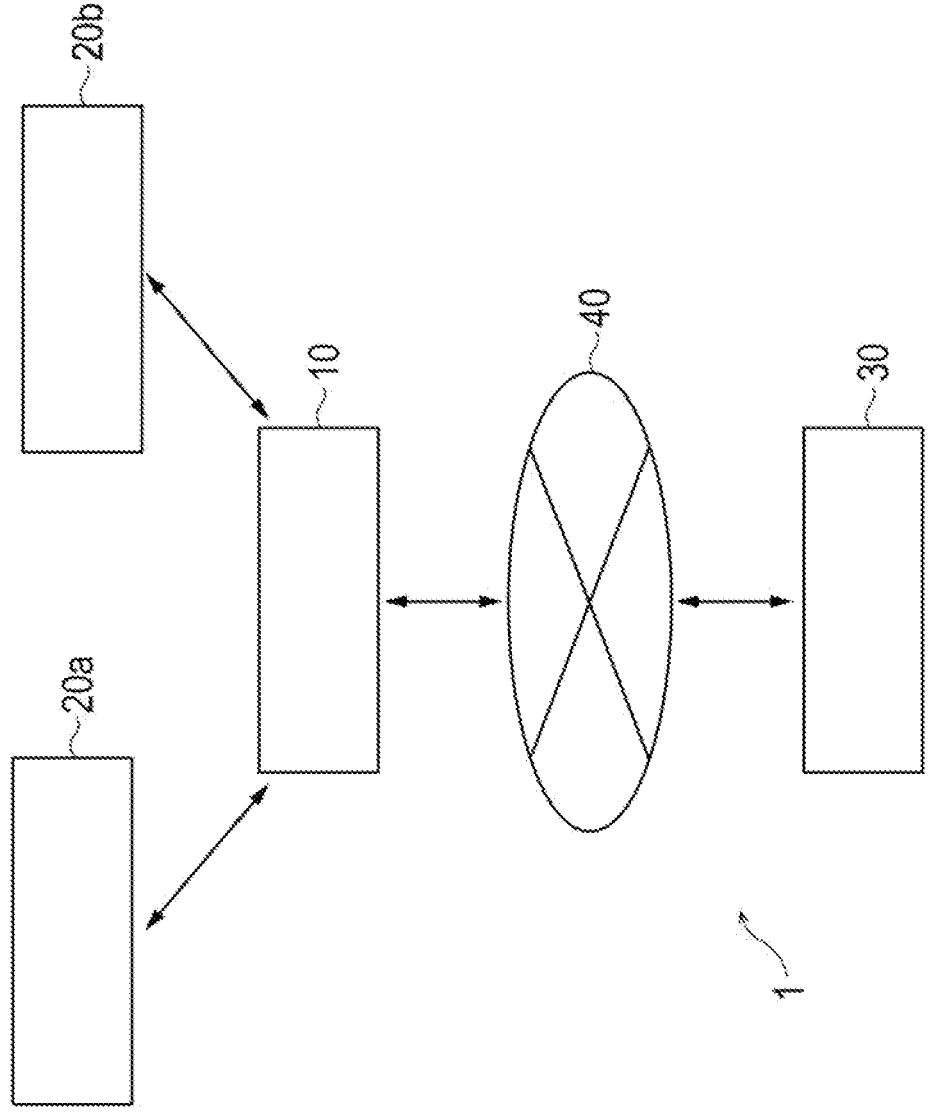

MEDICAL DEVICE HAVING COMMMUNICATION FUNCTION AND COMMUNICATION SYSTEM

CROSS-REFERENCES TO RELATED APPLICATIONS

This application is a continuation of International Application No. PCT/JP2021/002983 filed on Jan. 28, 2021, which claims priority to Japanese Application No. 2020-032305 filed on Feb. 27, 2020, the entire content of both of which is incorporated herein by reference.

TECHNOLOGICAL FIELD

The present disclosure relates to a medical device having a communication function and a communication system.

BACKGROUND DISCUSSION

In recent years, catheter robots are being developed for applications where a guide catheter, a guide wire, a balloon catheter, a stent, or other elongated medical instruments is inserted into a patient to perform surgical procedure (surgical manipulation) such as percutaneous coronary intervention (PCI).

Disclosed in Japanese Patent Laid-open No. 2017-205546 is an apparatus that includes a cassette coupled to an arm having multiple degrees of freedom for proper positioning with respect to a patient. The cassette includes a first axis drive mechanism, a second axis drive mechanism, and a first rotary drive mechanism. The first axis drive mechanism drives a guide wire along a longitudinal axis. The second axis drive mechanism drives a catheter device along the longitudinal axis. The first rotary drive mechanism rotates, for example, the guide wire around the longitudinal axis. Further, the cassette not only includes a radio frequency identifier (RFID) tag, but also includes means for providing unique descriptive information such as a type, features, and a unique identifier of the cassette, in order to distinguish the cassette from other cassettes.

Catheters, guide wires, and other medical instruments used for PCI or other surgical procedures are increasing in the number of varieties year after year. Further, the medical instruments used for various cases of illness differ in variety and use order. Therefore, if the variety or use order of a medical instrument becomes unclear during a surgery, a considerable amount of time and effort can be required to confirm the variety or the use order of the medical instrument.

Further, when making, for example, a catheterization record or a nursing record, healthcare workers might make a mistake regarding, for example, the size of a catheter or other devices used for surgical procedures and the anesthetic dose because the information is handwritten or such information is manually input into a personal computer. Particularly, for example, in an emergency at night, such information may be recorded by a person unfamiliar with medical practice such as PCI. Therefore, it is highly probable that the recorded information is unusual or erroneous.

Further, if a doctor in charge of medical practice inputs a report to an electronic medical record after a surgery according to the above-mentioned nursing record or the doctor's vague memory about the surgery, the report containing erroneous information might remain uncorrected in a hospital information system (HIS).

SUMMARY

The present disclosure provides a medical device having a communication function and a communication system that make it possible to accurately store medical information in a hospital information system.

According to an aspect of the present disclosure, there is provided a medical device having a communication function, which include an information reading section and a communication section. The information reading section is able to read, from an additional medical device, information regarding medical care. The communication section is able to transmit the information read by the information reading section.

According to another aspect of the present disclosure, a communication system including the above-mentioned device having a communication function, the above-mentioned additional medical device, and a hospital information system. The hospital information system stores information transmitted from the above-mentioned medical device having a communication function.

According to a further aspect of the present disclosure, a method for recording medical information includes reading information on one or more additional medical devices from an information embedding section attached to a main body of the one more additional medical devices or a package of the one or more additional medical devices; and transmitting the information read on the one or more additional medical devices to an information system.

The present disclosure makes it possible to transmit, for example, information regarding medical instruments and information regarding surgical procedures. Therefore, receiving, recording, and storing such information by the hospital information system helps eliminate the need for recording information by a manual input method used in the existing technology and helps increase the accuracy of the recorded information.

BRIEF DESCRIPTION OF THE DRAWINGS

FIG. 1 is a schematic diagram illustrating a configuration of a communication system according to an embodiment of the present disclosure.

DETAILED DESCRIPTION

Figure 2:
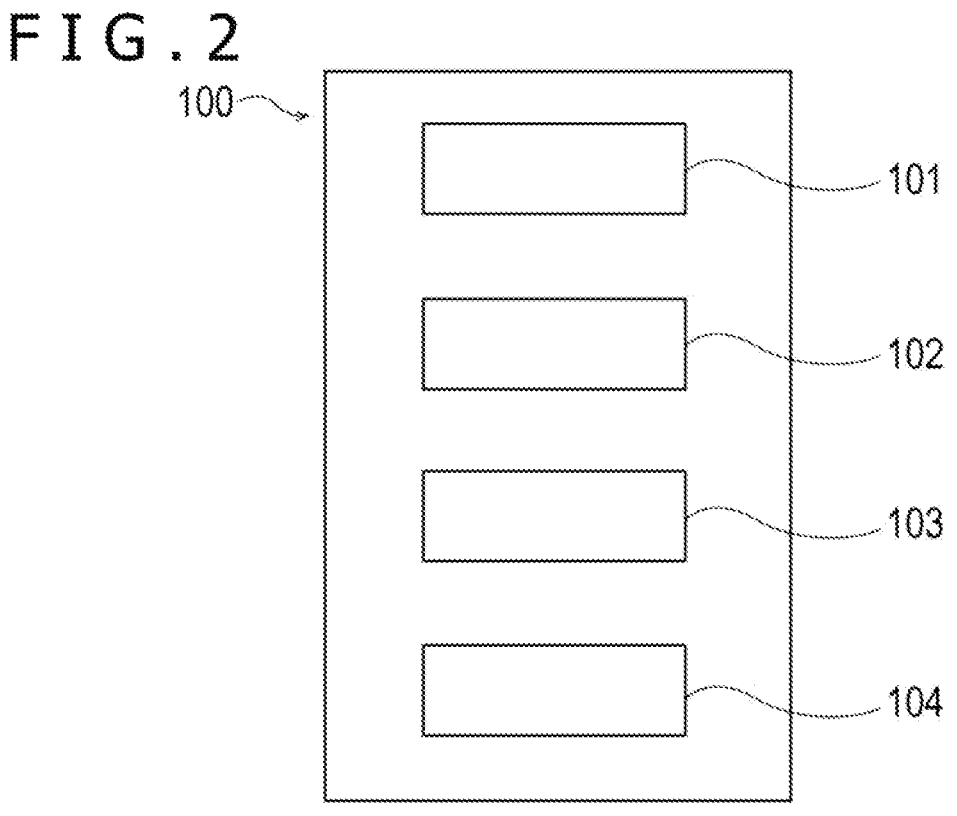
FIG. 2 is a block diagram illustrating an information reading apparatus.

Set forth below with reference to the accompanying drawings is a detailed description of embodiments of a medical device having a communication function and a communication system. Note that since embodiments described below are preferred specific examples of the present disclosure, although various technically preferable limitations are given, the scope of the present disclosure is not limited to the embodiments unless otherwise specified in the following descriptions.

FIG. 1 schematically illustrates a configuration of a medical system (corresponding to a "communication system") according to the preferred embodiment of the present disclosure. The medical system 1 includes a communication-capable medical device 10 (corresponding to a "medical device having a communication function" and hereinafter referred to as the "medical device 10"), additional medical devices (corresponding to "additional medical device having a communication functions") 20a and 20b different from the medical device 10, and a hospital information system (HIS) 30.

When, for instance, a surgery is performed in a surgery room, the medical device 10 and the additional medical devices 20a and 20b are used in the same surgery room. The medical device 10 and both of the additional medical devices 20a and 20b may include medical devices (medical equipment) used by healthcare workers and all various medical devices used for medical treatment. The medical device 10 can be, for example, a relatively long (or elongated) medical device such as a guide catheter, a guide wire, a balloon catheter, a stent, a drug bag used for medical practice such as PCI, or a catheter robot.

The present preferred embodiment will now be described with reference to an application example where the medical device 10 includes a Y-connector while the additional medical devices 20a and 20b each include a different type of guide wire.

The medical device 10 and the hospital information system 30 are connected to each other through a secure network 40. The hospital information system 30 can include a computer, and can include a hospital database for storing electronic medical records.

Figure 3:
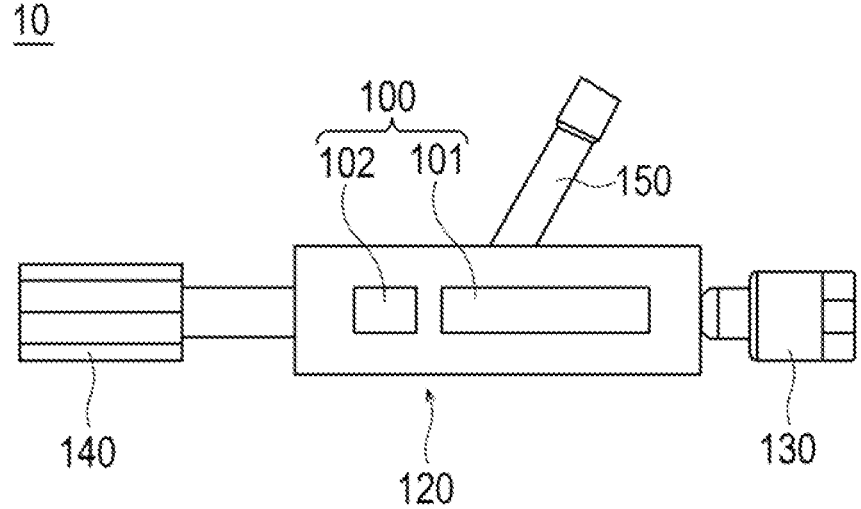
FIG. 3 is a front view of a medical device having a communication function including a Y connector.

FIG. 3 is a front view of the medical device 10.

When the medical device 10 is to be used, it is connected to a hub of a catheter. When connected to the hub, the medical device 10 is able to introduce, for example, a guide wire into the catheter.

The medical device 10 includes an information reading unit 100, a connector main body 120, a rotator 140, a cap 130, and a side tube 150. The rotator 140 is rotatably supported by the distal end side (patient side) of the connector main body 120. The cap 130 is disposed on the proximal end side (surgeon side) of the connector main body 120 to form a seal structure. The side tube 150 is branched (extending) from, for example, the middle of the connector main body 120.

The information reading unit 100 can be disposed on the lateral surface of the connector main body 120. The information reading unit 100 can include a reading section 101 and a display section 102.

When the medical device 10 including a Y-connector is used for a surgery, the additional medical devices 20a and 20b including, for example, guide wires are inserted into a bore of the connector main body 120. When the additional medical devices 20a and 20b are inserted as described above, the medical device 10 enables the reading section 101 to read operating information and positional information regarding the additional medical devices 20a and 20b. Further, the medical device 10 helps enable the reading section 101 to read information, for example, regarding the type and the amount of drug from a package of the drug administered through the side tube 150.

Alternatively, the medical device 10 may include, for example, a medical robot for operating a catheter and a guide wire. In such a case, the medical robot can include the reading section 101 that is able to read the results of operations of medical devices used for a surgery.

Further, as is the case with the additional devices 20a and 20b, the medical device having a communication function provided by the present disclosure is not limited to a medical device or medical equipment that is directly used for medical practice such as a surgery. The medical device having a communication function and/or the additional medical devices 20a and 20b may alternatively be an L-shaped stand, a U-shaped stand, a rack, an operating table, or other medical equipment. In a case where the medical device having a communication function and/or the additional medical devices 20a and 20b make it possible to acquire and communicate, for example, information regarding medical devices, information regarding operations of the medical devices in the middle of a surgery, and information regarding operations of a surgeon in the middle of the surgery, it is preferable that the medical device having a communication function and/or the additional medical devices 20a and 20b include, for example, medical devices used during the surgery, in order to make it relatively easy to acquire such information. However, even in a case where the medical device having a communication function and/or the additional medical devices 20a and 20b include, for example, the above-mentioned fixtures, the information regarding medical devices can be acquired with relative ease. Moreover, in a case where the above-described configuration is adopted, the information regarding the operations of a surgeon can be acquired by, for example, an imaging camera being disposed, for instance, on the fixtures. Furthermore, the number of medical devices 10 used per surgery and the number of additional medical devices that communicate with the medical devices 10 are not limited to two.

FIG. 2 illustrates a block configuration of the information reading apparatus 100. The information reading apparatus 100 includes the reading section 101, the display section 102, a display control section 103, and a communication section 104.

The reading section 101 can include at least any one of an RFID, a reader for reading a different integrated circuit (IC) tag, a one-dimensional barcode reader, or a two-dimensional barcode reader. The reading section 101 reads information from an information embedding section, for example, for an RFID tag, a one-dimensional barcode, or a two-dimensional barcode that is attached to the main body or package of the additional medical devices 20a and 20b. The reading section 101 may include operating means for operating a guide wire and a function for reading the result of surgical procedures through the use of the operating means.

The display section 102 can include a display apparatus such as a liquid-crystal display or a light emitting diode (LED) lamp. The display control section 103 can be a driver for controlling a display operation performed by the display section 102, and is particularly able to output a signal indicating the completion of information reading by the reading section 101 and display the information read by the reading section 101. The display section 102 may be controlled, for example, to illuminate yellow while the information is being read, illuminate blue when the information is normally read, and illuminate red when the information is not successfully read. Further, the display section 102 may be used as a user interface for receiving an input from a user.

The communication section 104 is a communication interface that is connected to the network 40, and is able to transmit and receive desired information to and from the hospital information system 30. More specifically, the communication section 104 is able to transmit the information read by the reading section 101 to the hospital information system 30 and conversely, receive information from the hospital information system 30, output the information to the display control section 103, and cause the display section 102 to display the information.

Figure 4:
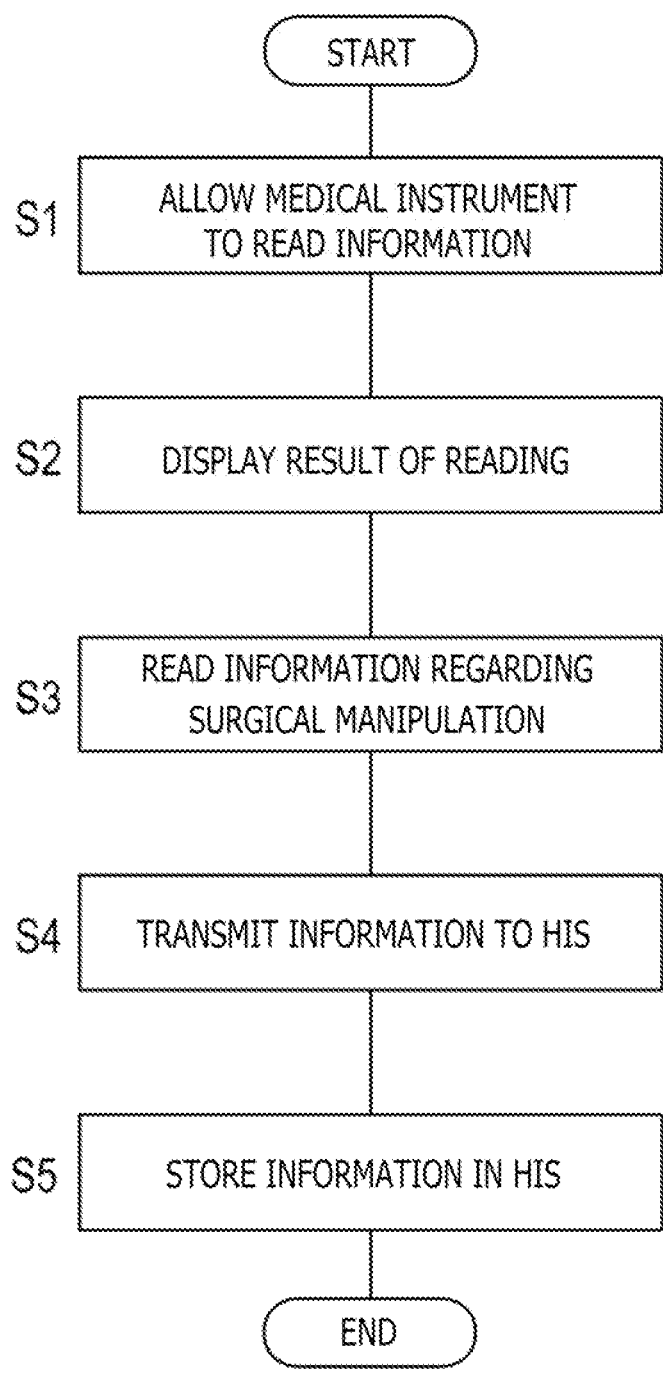
FIG. 4 is a flowchart illustrating a process performed by the communication system.

FIG. 4 is a flowchart illustrating a process performed by the medical system 1.

In S1, the reading section 101 of the medical device 10 reads information regarding the additional medical devices 20a and 20b, such as the information regarding a serial number, a product name, a type, usage precautions, and treatment outcomes of previous surgeries performed by using the medical devices, from the information embedding section attached to the main body or package of the additional medical devices 20a and 20b. Further, the reading section 101 is able to read information regarding the type and the amount of drug from a package of the drug administered through the side tube 150 of the Y-connector. It should be noted that all the above items of information need not be embedded in the information embedding section of the additional medical devices 20a and 20b. Alternatively, for example, a hyperlink may simply be embedded in the information embedding section so as to be able to acquire the above items of information, for instance, from a separate server.

In S2, the display control section 103 of the medical device 10 controls the display section 102 to display the result of reading.

In S3, the reading section 101 of the medical device 10 reads the result of surgical procedures (e.g., the back-and-forth movement in a longitudinal direction and the rotation around a longitudinal axis) from the guide wire, which is one of the additional medical devices 20a and 20b. Further, based on the order in which information has been acquired from the additional medical devices 20a and 20b, the medical device 10 additionally acquires information regarding, for example, a usage record and use order regarding surgical procedures.

In S4, the communication section 104 of the medical device 10 transmits the information read by the reading section 101 to the hospital information system 30.

In S5, the hospital information system 30 associates the items of information received from the medical devices 10 with each other, or more specifically, associates the information regarding the additional medical devices 20a and 20b, the information regarding the surgical procedure, and the information regarding administered drug with each other, and then stores the associated information in the hospital database.

For example, a nursing record regarding a patient can be stored in association with the information acquired by the medical device 10.

A plurality of the same type of medical devices 10 or a plurality of different types of medical devices 10 may be used for a surgery (a case of illness). For example, a plurality of medical devices (Y-connectors) can be simultaneously used in a surgery in which separate catheters are inserted into blood vessels of both arms. In such a case, each of the medical devices needs to be identified for data management purposes. For example, information regarding a puncture site (a blood vessel to which a medical instrument is connected) formed in a patient and information regarding the medical device used at the puncture site can be associated with each other and stored in the hospital database. Further, in a case where information is transmitted from a medical device, for example, to the hospital database, information identifying the medical instrument from which the information is transmitted can be included in the associated information to be stored. Additionally, not only the Y-connectors but also a plurality of trackers used for a laparoscopic surgery may be applied as the medical devices provided by the present disclosure.

As described above, the medical system 1 is able to automatically cause the hospital information system 30 to store the information regarding the medical devices used for medical practice on a patient and the information regarding surgical procedures, which helps save the healthcare workers from having to record information by using a manual input method used in the existing technology or by relying on their memory, and thus increases the accuracy of recorded information.

The medical device having a communication function and communication system according to the preferred embodiment of the present disclosure have been described in this document. However, the present disclosure is not limited to the preferred embodiment described in this document. Various modifications can be made by persons skilled in the art without departing from the scope of the appended claims.

The detailed description above describes embodiments of a medical device having a communication function and a communication system. These disclosed embodiments represent examples of the medical device having a communication function and the communication system disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device with a communication function, the medical device comprising:
   an information reading section configured to read, from an additional medical device, information regarding medical care;
   a communication section configured to transmit the information read by the information reading section; and
   wherein the medical device is a guide catheter, a guide wire, a balloon catheter, a stent, a drug bag used for medical practice, or a catheter robot.

2. The medical device according to claim 1, wherein the medical device is capable of being used for a surgical procedure.

3. The medical device according to claim 1, further comprising:
   a display section; and
   a display control section configured to control the display section to display the information read by the information reading section.

4. The medical device according to claim 1, wherein the communication section is configured to transmit, to a hospital information system, the information read by the information reading section.

5. The medical device according to claim 1, wherein the information reading section includes at least one of an integrated circuit tag reader, a one-dimensional barcode reader, and a two-dimensional barcode reader.

6. The medical device according to claim 1, wherein the information contains information regarding the additional medical device and the medical device.

7. The medical device according to claim 6, wherein the information contains information regarding a surgical procedure performed with the additional device.

8. The medical device according to claim 6, wherein the information contains information regarding treatment outcomes of previous surgeries performed by using the additional device.

9. The medical device according to claim 1, further comprising:

a connector main body;

a rotator rotatably supported by a distal end side of the connector main body;

a cap configured to be disposed on a proximal end side of the connector main body;

a side tube extending from the connector main body; and wherein the information reading section is disposed on a lateral surface of the connector main body.

10. The medical device according to claim 1, further comprising:

a Y-connector, and the additional medical device comprise two additional medical devices, which are different types of guide wires.

11. A communication system comprising:

the medical device of claim 1;

the additional medical device;

a hospital information system configured to store information transmitted from the medical device.

12. The communication system according to claim 11, further comprising:

an information embedding section including at least one of an integrated circuit tag, a one-dimensional barcode, and a two-dimensional barcode is attached to the additional device.

13. A medical device with a communication function, the medical device comprising:

an information reading section configured to read, from an additional medical device, information regarding medical care; and a communication section configured to transmit the information read by the information reading section, wherein the medical device is configured to be connected to a hub of a catheter, and configured to introduce a guide wire into the catheter.

14. A medical device with a communication function, the medical device comprising:

an information reading section configured to read, from an additional medical device, information regarding medical care;

a communication section configured to transmit the information read by the information reading section;

a connector main body;

a rotator rotatably supported by a distal end side of the connector main body;

a cap configured to be disposed on a proximal end side of the connector main body; and a side tube extending from the connector main body, wherein the information reading section is disposed on a lateral surface of the connector main body.

15. A medical device with a communication function, the medical device comprising:

an information reading section configured to read, from additional medical devices, information regarding medical care;

a communication section configured to transmit the information read by the information reading section; and a Y-connector, wherein the additional medical devices are different types of guide wires.

* * * * *